(12) United States Patent
Guinan et al.

(10) Patent No.: US 6,893,416 B2
(45) Date of Patent: May 17, 2005

(54) TIP SEAL TIP ATTACH

(75) Inventors: Terry Guinan, Galway (IE); John Connolly, Galway (IE); Pat Duane, Galway (IE); Donagh O'Shaughnessy, Galway (IE); Michael Bannon, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 382 days.

(21) Appl. No.: 09/881,080

(22) Filed: Jun. 12, 2001

(65) Prior Publication Data

US 2002/0188312 A1 Dec. 12, 2002

(51) Int. Cl.[7] .............................................. A61M 29/00
(52) U.S. Cl. .................................................. 604/96.01
(58) Field of Search ............................. 604/96.01, 523, 604/524, 525, 103; 156/272.8

(56) References Cited

U.S. PATENT DOCUMENTS

| | | |
|---|---|---|
| 4,782,834 A | 11/1988 | Maguire et al. |
| 4,921,483 A | 5/1990 | Wijay et al. |
| 5,254,090 A | 10/1993 | Lombardi et al. |
| 5,267,959 A | 12/1993 | Forman |
| 5,279,561 A | 1/1994 | Roucher et al. |
| 5,324,259 A * | 6/1994 | Taylor et al. ............. 604/99.04 |
| 5,425,712 A | 6/1995 | Goodin |
| 5,458,639 A | 10/1995 | Tsukashima et al. |
| 5,498,377 A | 3/1996 | Ozaki et al. |
| 5,501,759 A | 3/1996 | Forman |
| 5,509,910 A | 4/1996 | Lunn |
| 5,545,138 A | 8/1996 | Fugoso et al. |
| 5,545,200 A | 8/1996 | West et al. |
| 5,569,196 A | 10/1996 | Muni et al. |
| 5,569,221 A | 10/1996 | Houser et al. |
| 5,571,073 A | 11/1996 | Castillo |
| 5,643,209 A * | 7/1997 | Fugoso et al. ................. 604/96 |
| 5,667,493 A | 9/1997 | Janacek |
| 5,728,063 A | 3/1998 | Preissman et al. |
| 5,769,819 A | 6/1998 | Schwab et al. |
| 5,792,124 A | 8/1998 | Horrigan et al. |
| 5,811,043 A | 9/1998 | Horrigan et al. |
| 5,851,464 A | 12/1998 | Davila et al. |
| 5,882,336 A | 3/1999 | Janacek |
| 5,891,110 A | 4/1999 | Larson et al. |
| 5,911,715 A | 6/1999 | Berg et al. |
| 5,938,653 A | 8/1999 | Pepin |
| 5,964,778 A | 10/1999 | Fugoso et al. |
| 5,980,531 A | 11/1999 | Goodin et al. |
| 6,010,521 A | 1/2000 | Lee et al. |
| 6,030,405 A | 2/2000 | Zarbatany |
| 6,059,769 A | 5/2000 | Lunn et al. |
| 6,113,579 A | 9/2000 | Eidenschink et al. |
| 6,139,525 A | 10/2000 | Davis-Lemessy et al. |
| 6,165,166 A | 12/2000 | Samuelson et al. |
| 6,213,974 B1 | 4/2001 | Smith et al. |
| 2002/0082549 A1 * | 6/2002 | Duchamp ................. 604/96.01 |

FOREIGN PATENT DOCUMENTS

EP 0 742 029 A1 11/1996

* cited by examiner

*Primary Examiner*—Henry Bennett
*Assistant Examiner*—Andrea M. Ragonese

(57) ABSTRACT

The present invention is a catheter having an elongated tubular member having a proximal and a distal end. A balloon is positioned at the distal end of the tubular member. A guidewire tubular member extends from a position proximal the balloon through the balloon to a position distal the balloon, the guidewire tubular member has a proximal segment having a first flexibility and a distal segment having a second flexibility. The distal segment is more flexible than the proximal segment. A bond joins the balloon distal end to the proximal segment and the distal segment.

5 Claims, 2 Drawing Sheets

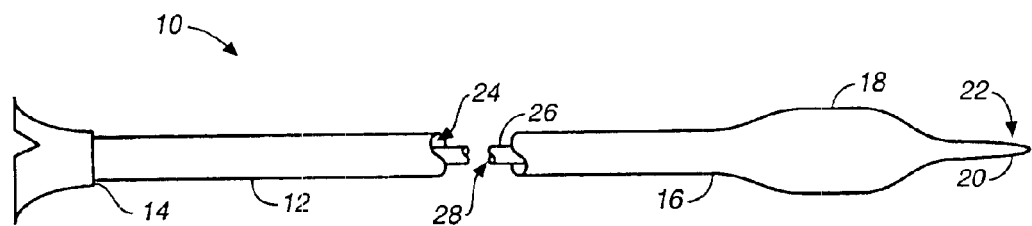
FIG._1
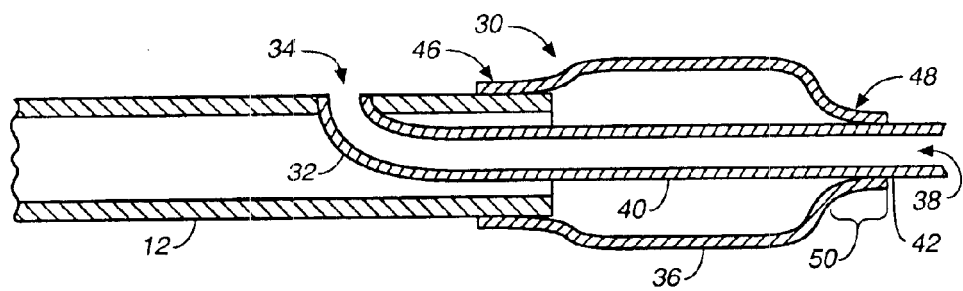
FIG._2
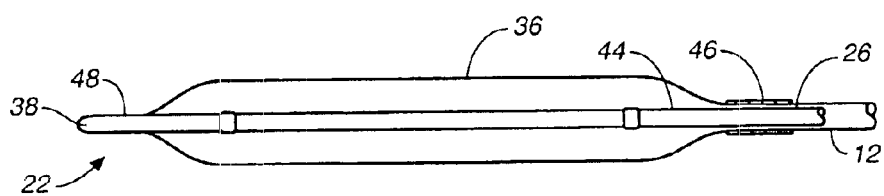
FIG._3

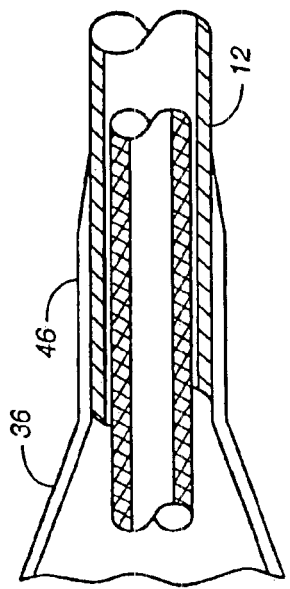
FIG._4
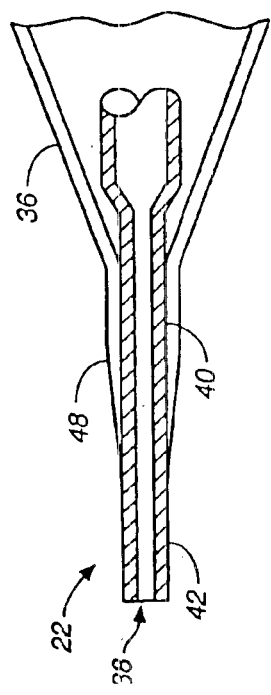
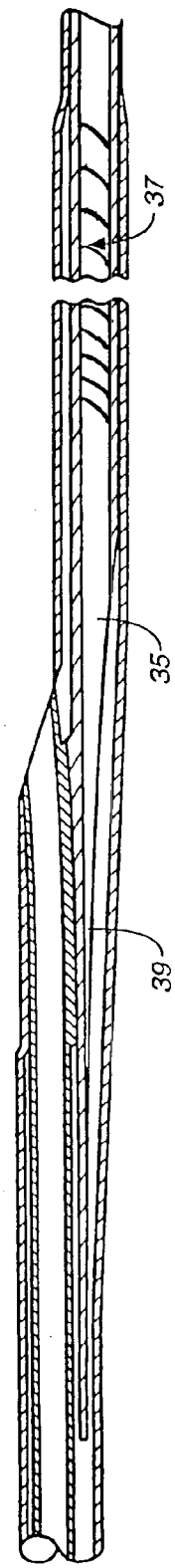
FIG._5

TIP SEAL TIP ATTACH

FIELD OF INVENTION

The present invention relates to a catheter and more importantly to the distal configuration of an intravascular catheter.

BACKGROUND OF THE INVENTION

Non-invasive procedures such as percutaneous transluminal angioplasty (PTA), percutaneous transluminal coronary angioplasty (PTCA), stent delivery and deployment, radiation treatment, delivery of a drug at a lesion site and other procedures are used in the treatment of intravascular disease. These therapies are well known in the art and most utilize a balloon catheter in conjunction with a guidewire. First, a guidewire is advanced in the patient until it reaches the treatment site at the lesion or stenosis. The balloon catheter is then advanced over the guidewire until it reaches the treatment site. The balloon is inflated to compress the lesion site and dilate the previous narrowed lesion or stenosis site. If the balloon carried a stent or drug, the drug or stent is delivered at the site when the balloon is inflated. Likewise additional therapies may use a balloon catheter in the treatment of the lesion site.

Catheters used in vascular procedures must be flexible to navigate the tortuous anatomy of the patient's vasculature, but must also have sufficient stiffness to aid in pushability and tracking of the catheter. As a result, catheters have been designed to have a more flexible distal end and a stiffer proximal portion. However, there continues to be a need for a catheter with an extremely flexible tip that does not diminish trackability of the catheter. The present invention addresses this need by providing a novel way to attach a flexible distal tip without diminishing from the tracking and pushability of the catheter.

SUMMARY OF THE INVENTION

The present invention is a balloon catheter that includes an elongated tubular member having a proximal and a distal end. A balloon is positioned at the distal end of the tubular member. The elongated tubular member has a proximal segment that comprises much of the length of the catheter. A distal segment begins proximal of the balloon and extends past the balloon forming the tip. An inflation lumen extends through the elongated tubular member for providing an inflation fluid for the balloon.

The catheter also includes a guidewire tubular member. The catheter may be an over the wire catheter type in which the guidewire tubular member extends from a luer on the proximal end of the catheter through the length of the catheter to the distal tip of the catheter. Alternatively, the catheter may be of a rapid exchange type. In this design, the guidewire tubular member extends from a position proximal the balloon through the balloon to a position distal the balloon. The guidewire tubular member has at least two segments. A proximal segment has a first flexibility and a distal segment has a second flexibility. The distal segment is more flexible than the proximal segment.

The balloon is bonded at its proximal portion to the proximal tubular member in a conventional manner with either an adhesive or heat/fusion bond. A fusion or heat bond joins the balloon distal end to the proximal segment and the distal segment of the distal tubular member.

BRIEF DESCRIPTION OF THE DRAWINGS

The novel features of the invention, as well as the invention itself, both as to structure and operation, will be best understood from the accompanying drawings, taken in conjunction with the accompanying description:

FIG. 1 is a segmented side elevational view of a catheter of the present invention;

FIG. 2 is a sectional view of the distal portion of the catheter of the present invention;

FIG. 3 is a sectional side view of the balloon portion of the catheter of the present invention;

FIG. 4 is another partial sectional view of the balloon portion of the catheter of the present invention; and FIG. 5 is a partial sectional view of the exchange joint of the catheter of the present invention.

DETAILED DESCRIPTION OF THE INVENTION

The present invention is shown generally as catheter 10 in FIG. 1. It includes an elongated catheter body 12 with a proximal end 14 and a distal end 16. A conventional luer (not shown) is located at proximal end 14. Balloon 18 is positioned approximate the distal portion of catheter body 12, with tip 20 extending distally from balloon 18 forming distal end 22 of catheter 10. Balloon 18 may be used for angioplasty, deployment of a stent, delivery of a drug or other vascular procedures requiring a balloon catheter.

Catheter body 12 defines an inflation lumen 24 that extends from the luer where it is attached to an inflation source during a procedure to balloon interior. A second tubular body 26 defines a guidewire lumen 28. As shown in FIG. 1, second tubular body 26 extends through the elongated catheter body 12 and balloon 18, with its tip forming the distal end 22 of catheter 10 for an over the wire catheter. While not shown, the elongated catheter may have a region of intermediate stiffness between the proximal portion of catheter 10 and the distal portion of catheter 10. Alternatively, the guidewire tubular body 26 may be shorter than the elongated catheter body 12 if the catheter has a rapid exchange configuration.

FIG. 2 shows a distal portion of a catheter 30 with a rapid exchange configuration. As shown, guidewire tubular body 32 has an entrance port 34 proximal of balloon 36 and it extends through balloon 36 terminating at exit port 38. Guidewire tubular body 32 has a proximal segment 40 that is preferably constructed of a trilayer of high density polyethylene (HDPE)/binder layer (e.g. Plexar® Resin)/polyether-block co-polyamide polymer (Pebax® 6333). Distal segment 42 of guidewire tubular body 32 is a single layer preferably constructed of Pebax® 7033. This material is more flexible than the material in the proximal portion. While these materials were selected, any other comparable materials may be used such as Pebax® 6333, 4033 and 5033. Guidewire tubular body 26 of the over the wire configuration likewise has a proximal segment 44 made of HDPE/Plexar® Resin/Pebax® 6333 and a distal segment forming tip 22 made of Pebax® 7033.

Another rapid exchange configuration is shown in FIG. 5. In this arrangement, the proximal segment of the catheter includes a skived hypotube 35. As seen in the figure, hypotube 35 has helical slits, designated 37, formed proximal the skived portion 39 of the hypotube. The slits may begin up to about 10 mm from the skived portion, although any suitable length may be used to ensure maximum performance of the catheter. Preferably the pitch of the helical configuration changes along the length of the slits, such as from a proximal pitch of 8.5 mm to about 0.8 mm at the distal portion of the slits.

Balloon 36, as shown in FIGS. 2, 3 and 4 has a proximal end 46 that is bonded to the elongated tubular body 12 forming a bond. This is a conventional bond such as a fusion bond, adhesive bond or other suitable bond. Distal end 48 of balloon 36 is likewise bonded to the guidewire tubular body 32. The bond is located in the area designated 50 in FIG. 2 so that balloon 36 is bonded to both proximal segment 40 and distal segment 42 of guidewire tubular body 32. The bond is formed in the following steps.

In the preferred bonding process, a mandrel is inserted through the guidewire tubular body, with the proximal segment and the distal segment in abutting relationship. The distal portion of the balloon is positioned over the abutting segments and then joined using heat or adhesive. In the case of a heat bond, a laser or RF source may be applied, fusing the balloon, proximal segment and distal segment together.

It is understood that the particular embodiments described herein are merely illustrative of the preferred embodiments of the present invention and that no limitations are intended to the details of construction or design herein shown other than as described in the appended claims.

What is claimed is:

1. A catheter comprising:

an elongated tubular member having a proximal end and a distal end;

a balloon positioned at the distal end of the tubular member, the balloon having a distal end;

an inflation lumen extending through the elongated tubular member for providing an inflation fluid for the balloon;

a guidewire tubular member extending from a position proximal the balloon through the balloon to a position distal the balloon, the guidewire tubular member having a proximal segment formed of a first material having a first flexibility bonded to and a distal segment formed of a second material different from the first material and having a second flexibility; and a bond joining the balloon distal end to the proximal segment and the distal segment.

2. The catheter of claim 1, wherein the first material is a trilayer of high density polyethylene, a binder layer, and a polyether-block co-polyamide polymer.

3. The catheter of claim 1, wherein the second material is a polyether-block co-polyamide polymer.

4. The catheter of claim 1, further comprising an exit port proximal of a proximal end of said balloon, wherein said exit port provides access to said guidewire tubular member.

5. The catheter of claim 1, wherein the second flexibility is greater than the first flexibility.

\* \* \* \* \*